United States Patent [19]

Cole et al.

[11] 3,953,593

[45] Apr. 27, 1976

[54] ANTIBACTERIAL COMPOSITIONS

[75] Inventors: Martin Cole; Robert Sutherland, both of Dorking, England

[73] Assignee: Beecham Group Limited, Great Britain

[22] Filed: Sept. 13, 1974

[21] Appl. No.: 505,741

[30] Foreign Application Priority Data

Sept. 28, 1973 United Kingdom............... 45504/73

[52] U.S. Cl. .............................................. 424/114
[51] Int. Cl.² ......................................... A61K 35/00
[58] Field of Search ................................... 424/114

[56] References Cited

UNITED STATES PATENTS 3,157,639   11/1964   Doyle et al. ........................ 424/271

OTHER PUBLICATIONS

The Merck Index, 8th Ed., Merck & Co., Inc., Rahway, N.J., 1968, p. 222.

Primary Examiner—Jerome D. Goldberg

[57] ABSTRACT

Compositions containing a mixture of 2-isopropoxynaphth-1-yl penicillin and cephaloridine or cephalothin have been found to show enhanced activity against certain clinically important bacteria.

7 Claims, No Drawings

ANTIBACTERIAL COMPOSITIONS

The present invention relates to antibacterial compositions.

Several clinically important species of gram-negative bacteria show high degrees of resistance to penicillins and cephalosporins. It is believed that one frequent cause of such resistance to a β-lactam antibiotic is the production by the bacteria of considerable quantities of β-lactamases which are capable of opening the β-lactam ring present in the antibiotic thereby causing it to be degraded to an inactive material. One suggested method of overcoming this difficulty is to administer a β-lactamase inhibitor at the same time as the antibiotic. Unfortunately, this approach has not always proved satisfactory, for example O'Callaghan [Antimicrobial Agents and Chemotherapy, 2, 442 (1972)] points out that although nafcillin has a particularly broad spectrum of β-lactamase inhibition, combinations of nafcillin and cephaloridine were disappointing when tried against growing cells.

Cole et al. [Biochem. J., 127, 295 (1972)] showed that numerous penicillins were able to inhibit the effect of various β-lactamases and that one group of compounds having good inhibitory activity were derivatives of naphthylpenicillin of the formula (I):

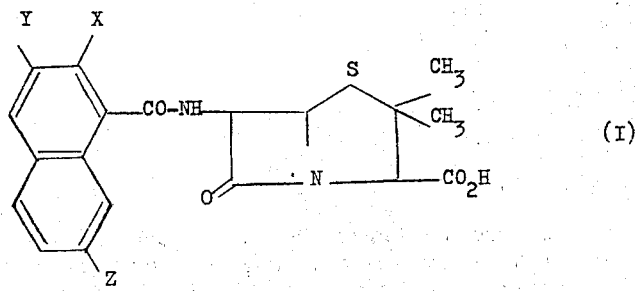

wherein X, Y and Z were hydrogen atoms or alkoxyl groups.

We have now found that one of the compounds of formula (I) is capable of enhancing the effectiveness of certain cephalosporins against several different gram-negative bacteria and against many β-lactamase producing strains of *E. coli* and *Klebsiella aerogenes*. No previous report has described such broad synergism.

The present invention provides a pharmaceutical composition which comprises a compound of the formula (II):

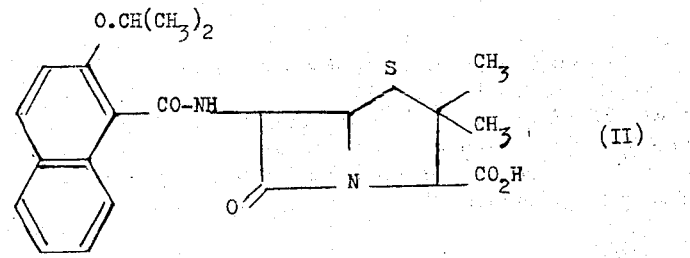

or a salt thereof together with either (*a*) cephaloridine or (*b*) cephalothin or a salt thereof; together with a pharmaceutically acceptable vehicle.

Neither the compound of formula (II) nor cephaloridine or cephalothin is well absorbed by the oral route so that the compositions of the invention are normally in a form suitable for administration by injection or infusion.

The composition may be in the form of any conventional injectable or infusable composition commonly used for the administration of poorly orally absorbed β-lactam antibiotics such as carbenicillin, cephalothin or cephaloridine.

A preferred embodiment of the composition of the invention comprises a mixture of an alkali metal salt of the compound of formula (II) with either cephaloridine or an alkali metal salt of cephalothin. The preferred alkali metal salts are the sodium salts.

The ratio of the compound of formula (II) to cephalothin or cephaloridine present in the composition may vary from 10 : 1 to 1 : 10. Preferred ratios are from 5 : 1 to 1 : 5.

When provided in pre-measured unit dosage form, the composition will normally contain from 100 mg. to 2g. of β-lactam antibiotic, more suitably, from 200 mg. to 1.5g., for example, 500 mg. to 1g.

This infection also describes a method of treating bacterial invention in humans which method comprises the administration of a compound of the formula (II) and the administration of cephalothin or a salt thereof or cephaloridine. The compounds may be administered separately or in admixture. Administration will normally and preferably be by injection or infusion. In general, from 100 mg. to 6000 mg. of antibiotic will be administered per day and usually in divided doses. Larger amounts may be used if required in accordance with conventional medical practice.

The following Examples illustrate the effectiveness of the compositions of the invention. The data relating to ampicillin is included by way of comparison only. BRL 1437 is the sodium salt of the compound of formula (II).

Synergism between the β-lactamase inhibitor BRL 1437 and cephaloridine or cephalothin against ampicillin resistant strains of Escherichia coli obtained from urinary tract infections Minimum inhibitory concentrations (μg/ml) determined by serial dilution in nutrient agar after overnight incubation at 37°C

| Strain of Escherichia coli | Ampicillin Alone | Ampicillin + 20 μg/ml BRL 1437 | Cephaloridine Alone | Cephaloridine + 20 μg/ml BRL 1437 | Cephalothin Alone | Cephalothin + 20 μg/ml BRL 1437 | BRL 1437 Alone |
|---|---|---|---|---|---|---|---|
| 79 | 250 | 100 | 50 | 5 | >1000 | 10 | 250 |
| 54 | 250 | 50 | 50 | 5 | 1000 | 5 | 250 |
| 6 | 250 | 100 | 100 | 25 | >1000 | 25 | 250 |
| 44 | 1000 | 250 | 100 | 25 | >1000 | 25 | 250 |
| 61 | 1000 | 250 | 10 | 2.5 | 10 | 2.5 | 250 |
| 90 | >1000 | >1000 | 50 | 10 | 50 | 10 | 250 |
| 97 | >1000 | 1000 | 50 | 10 | 25 | 10 | 250 |
| 7 | >1000 | 500 | 50 | 5 | 25 | 5 | 250 |
| 39 | >1000 | 100 | 10 | 2.5 | 25 | 2.5 | 250 |
| 45 | >1000 | 100 | 10 | 5 | 25 | 5 | 250 |

Synergism between the β-lactamase inhibitor BLR 1437 and cephalothin against ampicillin resistant strains of Klebsiella aerogenes obtained from urinary tract infections Minimum inhibitory concentrations (μg/ml) determined by serial dilution in nutrient agar after overnight incubation at 37°C

| Strain of Klebsiella Aerogenes | Ampicillin Alone | Ampicillin + 100 μg/ml BRL 1437 | Cephalothin Alone | Cephalothin + 100 μg/ml BRL 1437 | BRL 1437 Alone |
|---|---|---|---|---|---|
| 3 | 250 | 50 | 5 | <5 | >250 |
| 17 | >1000 | >1000 | 50 | 12.5 | >250 |
| 22 | 250 | 25 | 5 | <5 | >250 |
| 29 | >1000 | 1000 | 50 | 12.5 | >250 |
| 37 | >1000 | 500 | 25 | <5 | >250 |
| 40 | >1000 | 500 | 25 | <5 | >250 |
| 52 | >1000 | >1000 | 250 | 50 | >250 |
| 63 | 125 | 10 | 5 | <5 | >250 |
| 99 | >1000 | >1000 | 25 | 5 | >250 |

Frequency of synergism between BRL 1437 and cephaloridine or cephalothin against ampicillin and cephalosporin resistant strains of Gram-negative bacteria Number of strains showing suppression of growth for 20 hrs. or more in a broth culture system with 250 μg/ml of the following compounds in presence and absence of 250 μg/ml of BRL 1437. The numbers of bacteria tested are shown in brackets

| Strains of Bacteria | | Ampicillin | Cephaloridine | Cephalothin | Ampicillin + BRL 1437 | Cephaloridine + BRL 1437 | Cephalothin + BRL 1347 |
|---|---|---|---|---|---|---|---|
| Escherichia coli | (38) | 0 | 1 | 0 | 16 | 35 (37) | 38 |
| Klebsiella spp. | (19) | 0 | 0 | 3 | 1 | 11 | 10 (16) |
| Eutcrobacter | (4) | 0 | 0 | 1 | 0 | 3 | 2 |
| Proteus mirabilis | (8) | 0 | 1 | 1 | 7 | 7 (7) | 6 (7) |
| Serratia marcescens | (6) | 0 | 0 | 0 | 5 | 5 | 3 |
| % Strains showing synergism | | | | | 39% | 84% | 83% |

What we claim is:

1. An antibacterial pharmaceutical composition which comprises an antibacterially effective amount of a mixture of 2-isopropoxynaphth-1-yl pencillin, or a physiologically acceptable salt thereof, and cephaloridine, or a physiologically acceptable salt thereof, in a ratio of 2:1 to 1:2 in combination with a pharmaceutically acceptable vehicle.

2. An antibacterial composition according to claim 1 in a form suitable for injection or infusion.

3. An antibacterial composition according to claim 2 wherein 2-isopropoxynaphth-1-yl is in the form of its sodium salt.

4. An antibacterial composition according to claim 1 containing from 100 mg to 2 g of said mixture.

5. An antibacterial composition according to claim 4 containing from 500 mg to 1000 mg of said mixture.

6. A method of treating bacterial infection in humans which comprises administering to a human in need thereof an antibacterially effective amount of a mixture of 2-isopropoxynaphth-1-yl penicillin, or a physiologically acceptable salt thereof, and cephaloridine, or a physiologically acceptable salt thereof, in the ratio of 2:1 to 1:2.

7. A method of treating bacterial infection in humans which comprises administering to a human in need thereof by injection or infusion an antibacterially effective amount of a mixture according to claim 1.

* * * * *